United States Patent
Soliman

(10) Patent No.: US 8,936,600 B2
(45) Date of Patent: Jan. 20, 2015

(54) DRILL GUIDE WITH ANGLE VERIFICATION

(71) Applicant: Howmedica Osteonics Corp., Mahwah, NJ (US)

(72) Inventor: Mohamed Soliman, Englewood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/722,358

(22) Filed: Dec. 20, 2012

(65) Prior Publication Data

US 2013/0110117 A1    May 2, 2013

Related U.S. Application Data

(62) Division of application No. 12/317,703, filed on Dec. 23, 2008, now abandoned.

(51) Int. Cl.
*A61B 17/58*    (2006.01)
*A61B 17/60*    (2006.01)
*A61B 17/17*    (2006.01)
*A61B 19/00*    (2006.01)

(52) U.S. Cl.
CPC ....... *A61B 17/1728* (2013.01); *A61B 2019/467* (2013.01); *A61B 17/1739* (2013.01)
USPC ............. 606/96; 606/86 B; 606/102; 606/104

(58) Field of Classification Search
CPC ......... A61B 17/17; A61B 17/58; A61B 17/60
USPC ............. 606/53, 79, 80, 86 R, 87, 88, 89, 90, 606/96–99, 102, 104, 86 B; 408/241 B, 408/241 G, 241 S
See application file for complete search history.

(56) References Cited

U.S. PATENT DOCUMENTS

| | | | |
|---|---|---|---|
| 4,493,317 | A | 1/1985 | Klaue |
| 5,507,801 | A | 4/1996 | Gisin et al. |
| 6,673,115 | B2 | 1/2004 | Resch et al. |
| 7,094,242 | B2 | 8/2006 | Ralph et al. |
| 7,131,974 | B2 | 11/2006 | Keyer et al. |
| 7,357,804 | B2 | 4/2008 | Binder, Jr. et al. |
| 7,422,594 | B2 | 9/2008 | Zander |
| 7,488,327 | B2 | 2/2009 | Rathbun et al. |
| 2003/0083667 | A1 | 5/2003 | Ralph et al. |
| 2003/0233098 | A1 | 12/2003 | Markworth |
| 2007/0055286 | A1 | 3/2007 | Ralph et al. |
| 2007/0233150 | A1 | 10/2007 | Blain et al. |

*Primary Examiner* — Yashita Sharma
(74) *Attorney, Agent, or Firm* — Lerner, David, Littenberg, Krumholz & Mentlik, LLP

(57) ABSTRACT

A method and instrument is used for inserting a bone screw through a hole in a bone plate into bone at a maximum angulation of a bone screw central longitudinal axis with respect to a central axis of the hole. The maximum angulation places the head of the bone screw at or below an outwardly facing surface of the bone plate. The instrument has a distal end including a gauge element spaced proximally from an end surface of the distal end when in contact with a counterbore surrounding the plate hole a distance less than a depth of the counterbore. The instrument is tilted with respect to a central axis of the bone plate hole to an angle wherein the gauge element remains at or below the outwardly facing surface of the bone plate adjacent the counterbore. A hole is drilled through a guide bore in the instrument.

15 Claims, 6 Drawing Sheets

DRILL GUIDE WITH ANGLE VERIFICATION

CROSS-REFERENCE TO RELATED APPLICATION

The present application is a divisional of U.S. patent application Ser. No. 12/317,703, filed on Dec. 23, 2008, the disclosure of which is incorporated herein by reference.

BACKGROUND OF THE INVENTION

The invention relates to an angle guide for orienting a bone screw in a bone plate. More particularly, the invention relates to an instrument for insuring the position of the head of a bone screw located within a bone plate hole.

It is often necessary when utilizing bone plates either for fracture fixation or such as tibial base plates to couple the bone plates to bone via a screw extending through a hole in the plate. When the screw is angled, surgeons have had to eye the correct angle specified by the device manufacturer indicated by the surgical situation. If the bone screw is put in at too great an angle the bone screw head would sit proud of the bone plate which in some situations is undesirable. The surgeon would then either continue to torque the bone screw until the bone screw's cutting flutes soften the bone in the area and allowed it to sit properly or the bone screw would be backed out and the surgeon would attempt to reinsert the bone screw at a shallower angle.

The surgeon often had difficulty eyeing the correct angle especially where there was a plurality of bone screws to be inserted, since the correct angle is relatively small i.e. zero to ten degrees. Normally, the surgeon drills a pilot hole in the bone prior to inserting the bone screw and it has been difficult to drill the pilot hole at the correct angle so that the bone screw would seat properly. For example, when using a tibial base plate, it is typical to utilize a polyethylene bearing surface snapped onto the base plate which has been implanted on a prepared tibia. Consequently, if the pilot hole and subsequent bone screw are inserted at an incorrect angle the head of the bone screw could impinge on the distal surface of the polyethylene bearing implant which is undesirable. Such an impingement could lead to metal or polyethylene debris which has been known to cause osteolysis.

If the surgeon saw that the bone screw did not seat properly or was not at the specified depth, he could continue to torque the bone screw. However, since most bone screws include cutting flutes at the leading ends thereof continued rotation of the cutting flutes causes the bone to degrade and allows more play in the screws positioning. While this may allow the bone screw to seat properly, it reduces the compressive forces holding the plate to the bone by decreasing the holding ability of the screw.

Alternately, if the surgeon noticed the bone screw did not seat properly or is not at the correct depth, he might reverse the screw and drill a new pilot hole at a slightly different angle. This method may not always be successfully since the drill and screw will have a tendency to follow the original drilled hole. Even if the surgeon is capable of resetting the new desired angle, there is still damage to the bone in the originally drilled area which may cause fracture propagation. Consequently, there has been a long felt need to provide an instrument which can indicate the angle which is not to be exceeded for proper positioning of the bone screw in the bone plate. This instrument will verify that the final implant positioning is accurate and allows the head of the bone screw to be properly located.

BRIEF SUMMARY OF THE INVENTION

The instrument of the present invention is a drill guide for use in orthopedic surgery. It is intended to specify the maximum angle of a pilot hole drilled in bone when using bone screws for fixation of an orthopedic implant such as a bone plate. The instrument consists of several main features which include a handle which allows a surgeon to maneuver the instrument. A mating feature allows the device to interface with a corresponding implant, such as a bone plate, especially in an area surrounding a hole therein for accommodating a bone screw. This feature may be a part-spherical convex surface for rotating on a similar part-spherical concave surface surrounding the screw hole. A body having an appropriately sized through hole for guiding a drill and includes a circumferential visual reference delineating the amount of angulation a surgeon can put into a pilot hole drilled for receiving the bone screw.

The visual reference may be a reduction in diameter, a protrusion, an etched line or a laser marked line. Also color and surface finish could be used as visual indicators. Additionally, two or three visual references could be used indicating different angle markings i.e. 5°, 10° or 15°. Thus two or three lines could be used at different levels with the lower line corresponding to the greater angle. The visual reference may be observed by the surgeon and indicates to him that the pilot hole angle he or she is about to drill through the device is compatible with the orthopedic implant, such as a bone plate, and the bone screw securing it. The instrument allows the proper pilot hole angle to be drilled through the device and the implant and allows a bone screw to have the proper angulation and therefore seat properly within the recess hole in the device so that the bone screw head sits correctly in reference to the plate, or in the case of a tibial baseplate below the surface of the plate.

An instrument is provided for determining the position of a bone screw head with respect to a bone plate outer surface having a concave surface surrounding a screw hole in the plate. The instrument has a shaft having a leading end with a convex surface including a gauge element spaced from the end of the concave surface of the shaft. The gauge element is spaced a distance from the end surface of the shaft equal to or less than a distance from an outwardly facing surface of the bone plate, opposite a bone contacting surface, to the countersunk screw head seating surface surrounding the hole. Preferably the leading end of the shaft has a convex part-spherical portion for engaging a concave part-spherical countersunk surface on the bone plate. The gauge element is a mark extending around an outer circumference of the leading end of the shaft. The gauge element preferably is a circular line or indentation located intermediate the part-spherical portion and a cylindrical portion of the leading shaft end. The shaft leading end has a central bore therethrough for guiding a drill. The bore preferably has a central axis extending perpendicular to a plane containing the circumferential mark.

A method is taught for inserting a bone screw through a hole in a bone plate and into bone at a maximum angulation of a bone screw central longitudinal axis with respect to a central axis of the hole. The method includes placing a bone plate having at least one screw hole surrounded by a concave counterbore on an outwardly facing surface of the bone plate on a bone surface. Thereafter inserting the instrument having a distal end including the gauge element into the counterbore. The gauge element is spaced proximally from an end surface of the distal end. In one embodiment, the spacing is less than or equal to a distance from the counterbore surface to the outwardly facing surface of the bone plate. Alternatively, the gauge element can be greater than or equal to a distance from the counterbore surface to the outwardly facing surface of the bone plate. The instrument is tilted with respect to a central axis of the bone plate hole to an angle wherein the gauge element remains at or below the outwardly facing surface in the first scenario and at or above the bone plate in the second scenario. Then the hole is drilled in the bone through a guide bore in the instrument. The instrument is removed from the bone plate and the bone screw is inserted into the bone plate screw hole. The gauge element may be a circular ring mounted on the instrument on a circular line around the instrument. The tilting of the instrument is up to a maximum angle that maintains the circular ring or line at or below the outwardly facing surface of the bone plate surrounding the counterbore. Design intent guides the location of the gauge element from the distal end of the instrument which determines the corresponding maximum angle intended by the designer. An angled handle attached to the distal end of the instrument is used to tilt the distal end of the instrument. The distal end of the instrument is preferably part-spherical in shape matching the shape of the counterbore. The bore in the distal end extends perpendicular to a plane containing the gauge element.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body. When referring to the instrument, distal means further from the user.

BRIEF DESCRIPTION OF THE DRAWINGS

A more accurate appreciation of the subject matter of the present invention and the various advantages thereof can be realized by reference to the following detailed descriptions which makes reference to the accompanying drawings in which similar reference numerals relate to similar elements throughout several views.

DETAILED DESCRIPTION

Figure 1:
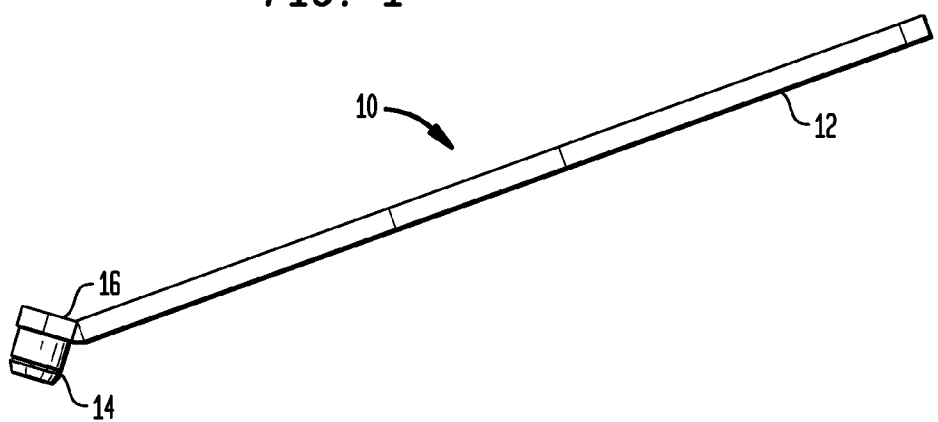
FIG. 1 is an isometric view of the instrument of the present invention from the side.
Figure 2:
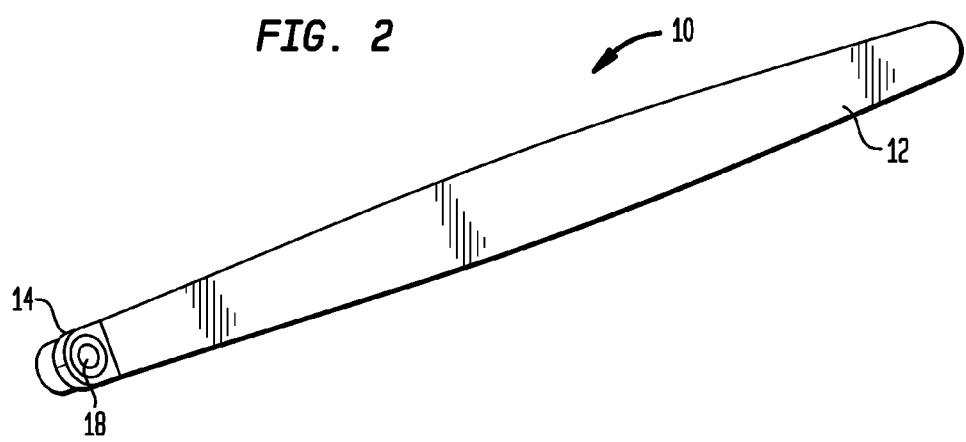
FIG. 2 is an isometric view of the instrument of the present invention from above with respect to FIG. 1.
Figure 4:
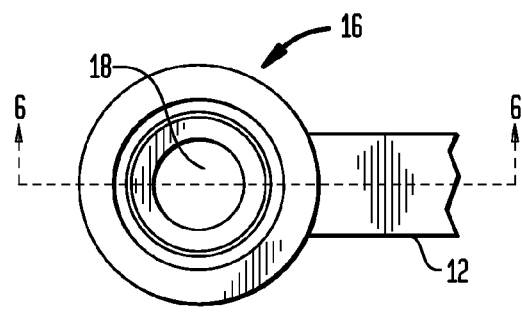
FIG. 4 is a top view of the tip of FIG. 3.
Figure 5:
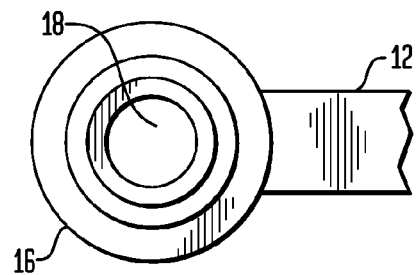
FIG. 5 is a bottom view of the instrument of FIG. 3.

Referring to FIG. 1, there is shown an isometric view of the instrument of the present invention generally denoted as 10. Instrument 10 includes a handle portion 12 and a leading or distal end 14 which includes a drill guide element 16 as can be seen in FIGS. 2, 4 and 5. Drill guide element 16 includes a guide bore 18. Guide bore 18 is adapted to receive a drill bit 20 such as shown in FIG. 9.

Figure 3:
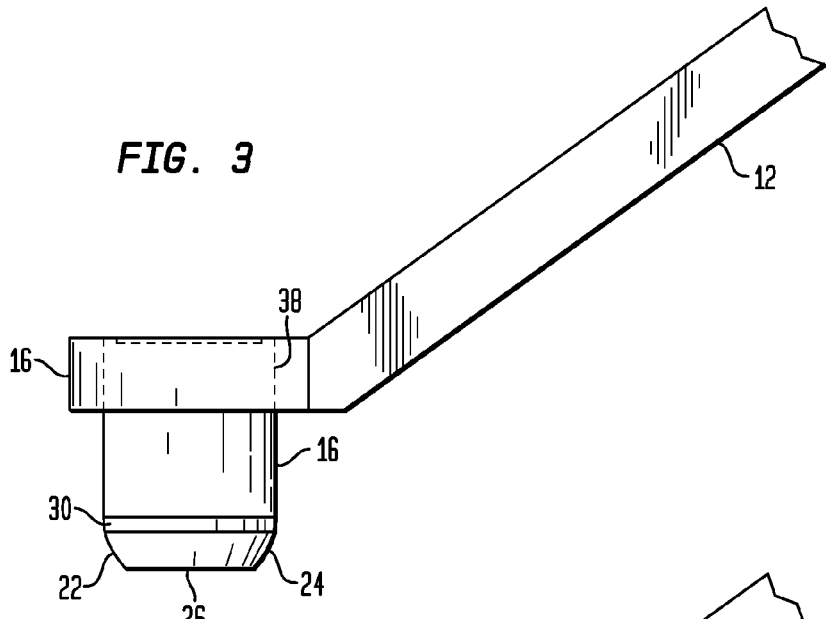
FIG. 3 is a side elevation view of the leading end of the instrument of FIG. 1.
Figure 3A:
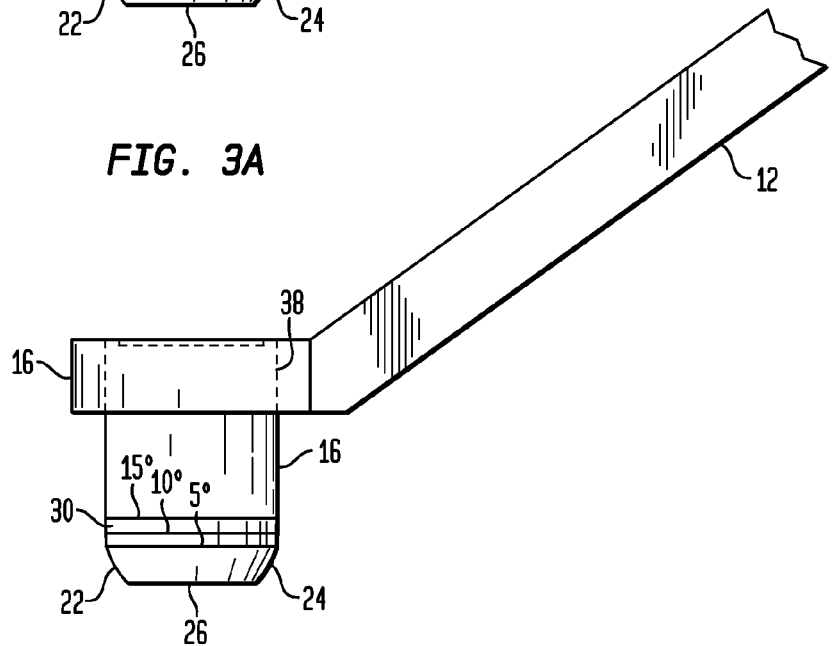
FIG. 3A is a side elevation view of the leading end of the instrument of FIG. 1 including three markings relating to a tilt angle of 5, 10 and 15 degrees.
Figure 8:
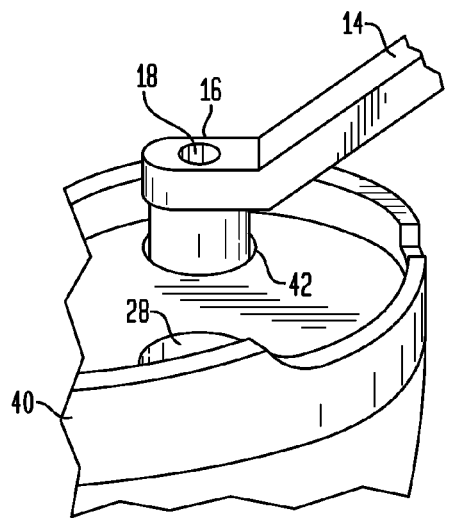
FIG. 8 shows the instrument of the present invention engaged in a tibial base plate mounted on a tibia.
Figure 9:
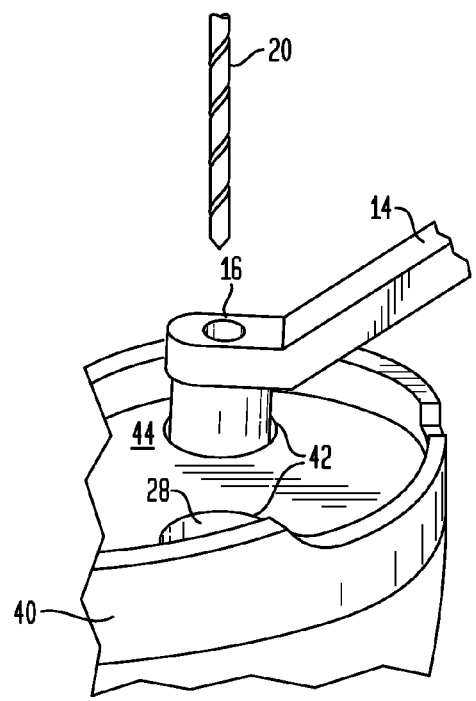
FIG. 9 shows the instrument of the present invention angled at a desired angle prior to inserting a drill for drilling a pilot hole.

Referring to FIG. 3, the drill guide element 16 has a leading end 22 which, in the preferred embodiment is cylindrical and includes a part-spherical convex contact surface 24 for engaging a part-spherical concave surface 28 surrounding a plate bore as shown in FIGS. 8 and 9. In the preferred embodiment, the element 16 includes a marking ring or line 30 which can be etched or laser marked or even being a groove of a reduced diameter in a predetermined axial location along the axial direction of element 16. The spacing of marking 30 with regard to end 26 of element 16 is determined by the design of recess 28 surrounding the hole in, for example, a tibial base plate and the size of the head of the bone screw. The location of marking 30 is such as to ensure that the head of the screw, after insertion at a desired angle, is below, above, or at the surface of the plate per the design intent.

Figure 6:
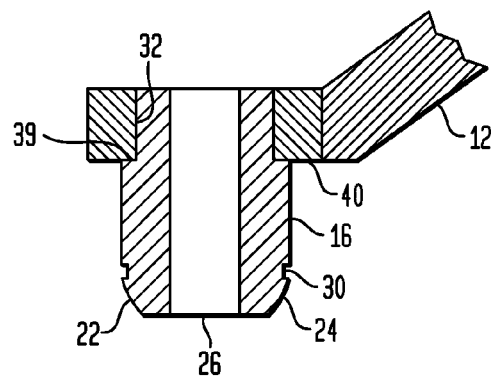
FIG. 6 is a cross-sectional view of the instrument of the present invention along lines 6-6 of FIG. 4.
Figure 7:
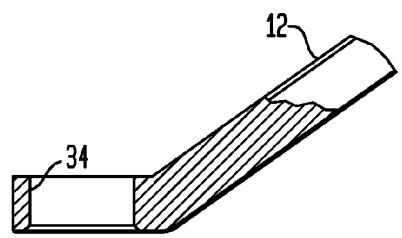
FIG. 7 is a cross-sectional view of the handle of the present invention separate from the bone plate engaging drill guide of FIG. 6.

In the preferred embodiment, as shown in FIGS. 6 and 7, the handle 12 is preferably made as a separate element which can be either permanently or releasably coupled to drill guide element 16. For example, drill guide element 16 could have a threaded portion 32 which could engage a threaded portion 34 in a bore 38 of handle 12. Thus, element 16 could be screwed into the handle prior to use. Obviously, a plurality of elements 16 having different size surfaces 24 could be provided as a kit to engage with a multiplicity of bone plate hole designs of various thicknesses and counterbores.

Again referring to FIG. 6, a stop surface 39 on element 16 sets the distance from a bottom surface 40 of handle 12 can be set to a desired length. Preferably the outer surface of locking element 16 is cylindrical and has a diameter equal to or less than the diameter of the opening or counterbore in the bone plate or other device adjacent its outwardly facing surface.

Referring to FIGS. 8 and 9, there is shown a tibial base plate 40 which includes a pair of bores 42 which, in the preferred embodiment, each are surrounded by a recessed part-spherical surface 28 matching the part spherical surface 24 on drill guide element 16.

As can be seen in FIGS. 8 and 9, pilot holes may be drilled with drill 20 which, in the preferred embodiment, may be a ⅛ inch drill so that pilot holes may be drilled through the tibial base plate screw holes. The pilot holes can be angulated up to ten degrees if a surgeon desires cortical fixation of the screws. The maximum allowable angulation of the screw is indicated by the drill guide. The bottom marking 30 of the drill guide 16 should not be visible when drilling a pilot hole. This ensures that the angulation is no more than ten degrees. If the marking is visible while drilling the pilot hole, as shown in FIG. 9, the screw head (not shown) may sit proud of the base plate outer surface 44. As described above, this could interfere with the polyethylene bearing element that would be received within the tibial base plate 40.

Alternately, as will be described below, a protrusion, such as a ring, may protrude outwardly from the distal instrument tip to provide a tactile reference for the surgeon to know that the device is at or past its maximum angle. For example, an embodiment having a hard stop may be provided for limiting the maximum angle but allowing freedom to position the device until that angle is reached. These features can be put on a spherical or non-spherical drill guide that is meant to enter a spherical or non-spherical hole. A spherical drill guide can be matched with a non-spherical hole or visa-versa if desired.

Figure 10:
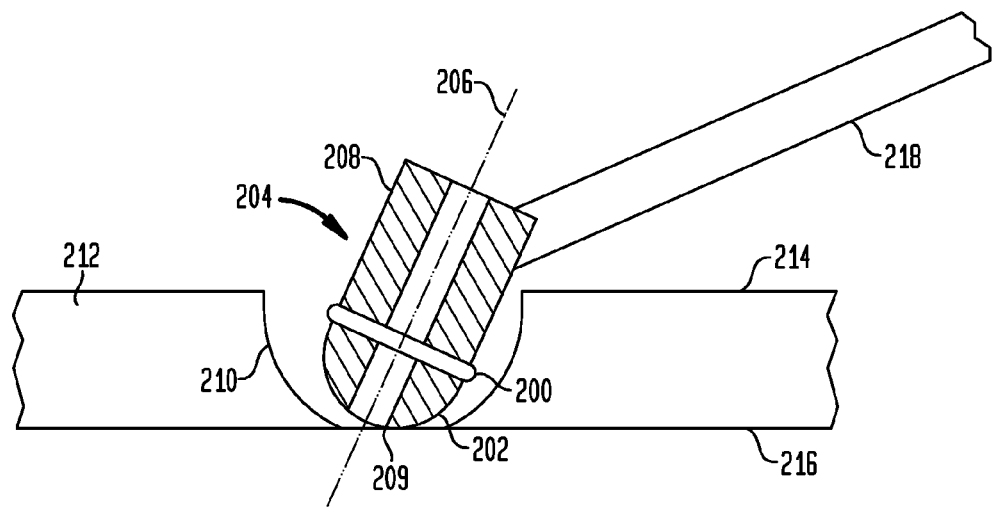
FIG. 10 is a cross-sectional view of an alternate embodiment of the present invention.

Referring to FIG. 10 there is shown a drill guide 204 within a hole in a bone plate 212 having a tactile feature in the form of a protruding ring 200 around the outer surface of the drill guide. The ring 200 is located distally on a shaft 202 of drill guide 204. Thus, when an axis 206 of the drill guide 204 is coaxial with an axis 208 of a hole 209 having a countersunk bore 210 in plate 212 ring 200 sits below a top surface 214 of bone plate 212 opposite a bone contacting surface 216 thereof. As protruding ring 200 engages the wall of the counter sunk bore 210 it causes a drag as the drill guide element 204 is moved via movement of a handle 218. This drag is felt by the surgeon and is a tactile indication of the acceptability of the drill guide position. Once the protruding ring 200 engages the wall of the counter sunk bore 210 the surgeon will feel this and know that the drill guide shaft 204 is at its maximum angle. The maximum diameter of protruding ring 200 is sized in conjunction with the countersunk bore 210 dimensions to produce such an effect.

Figure 11:
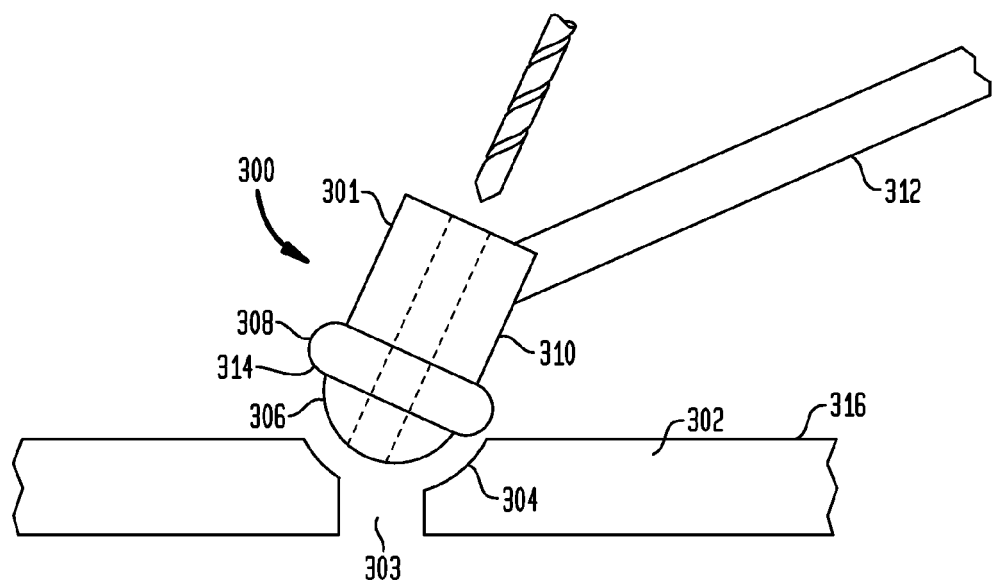
FIG. 11 is a cross-sectional view of yet another embodiment of the present invention.

Referring to FIG. 11 there is shown an alternate embodiment in which a drill guide 300 has a drill guide element 301 located in a counterbore 304 of a bone plate 302. Counterbore 304 surrounds a hole 303 in bone plate 302 for receiving a distal end 306 of drill guide 300. A ring-like protrusion 308 is provided. Protrusion 308 is located on a shaft 310 of drill guide element 301 in a proximal distal location so that when the drill guide is rotated via handle a 312 a bottom surface 314 of ring 308 contacts upper surface 316 of plate 302. In this design, protrusion 308 exhibits a tactile indication of the maximum angle to the surgeon as well as a hard stop surface. The preferred hard stop style drill guide formed by protrusion 308 is an increased radius or collar around the drill guide. As the drill guide is rotated in the counterbore 304 the protruding ring provides an indication of the maximum angulation the drill guide may take before the screw head protrudes above surface 316. When the drill guide is rotated by the surgeon to the point where the protrusion 308 contacts upper surface 316 of plate 302 the surgeon will be prevented from any further increase in the angle of the drill guide. In the preferred embodiment a circular protrusion is provided to ensure that the drill guide can be angulated in any direction with respect to the central axis of the hole 303 in plate 302.

Figure 12:
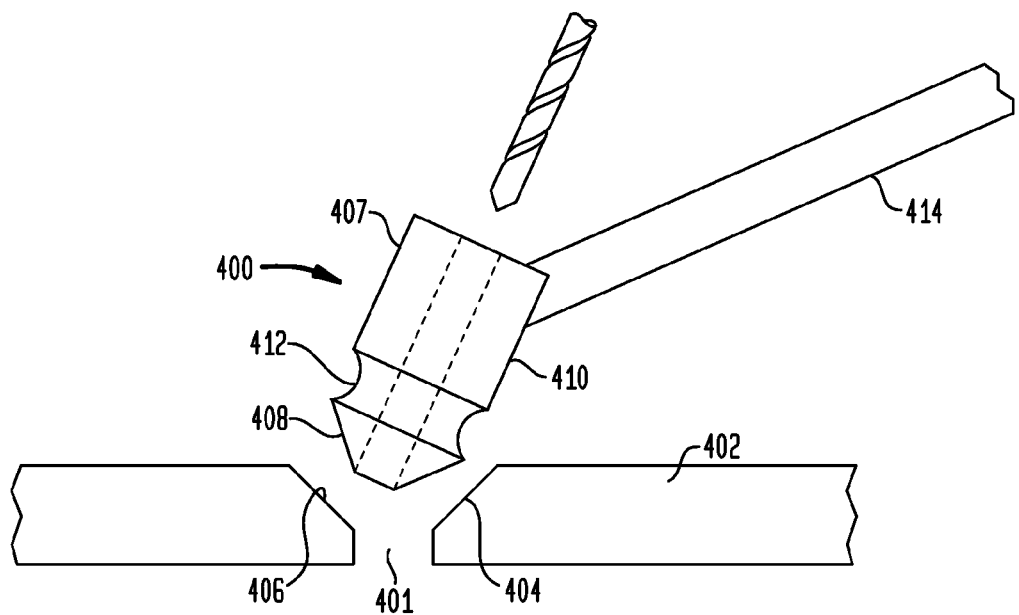
FIG. 12 is a cross-sectional view of a further embodiment of the present invention.

Referring to FIG. 12, there is shown a cross-sectional view of a drill guide 400 located in a hole 401 in plate 402. In this embodiment plate 402 has a counterbore 404 which has a conical surface 406. Drill guide 400 includes a drill guide element 407 having leading or distal end 408 on a shaft 410. Preferably end 408 is conically tapered, however, the leading end 408 can also be part-spherical or, for that matter, any shape which will allow the drill guide to pivot within the counterbore 404 of plate 402. A groove 412 may be provided to give a visual indication of the maximum angle that a handle 414 may be oriented to allow drilling of the pilot hole. A protrusion as discussed above may also be used.

Figure 13:
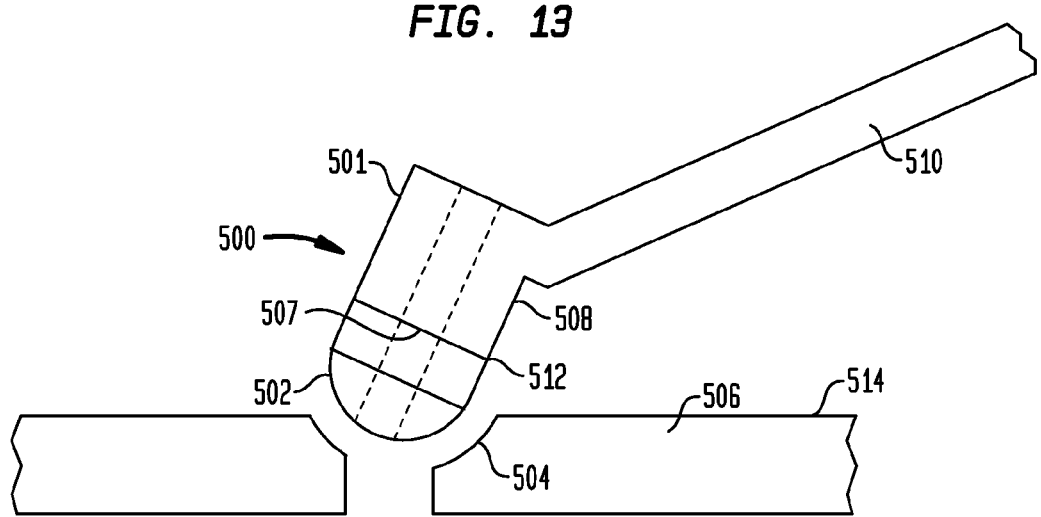
FIG. 13 is a cross-sectional view of an additional embodiment of the present invention.

Referring to FIG. 13 there is shown an embodiment similar to the embodiment of FIGS. 1-9 wherein a drill guide 500 is provided which includes a drill guide element 501 which has a part-spherical tip 502 for receipt in a counterbore 504 of a bone plate 506. Rather than a groove as shown in FIG. 6 a shaft 508 of drill guide element 501 includes a marking line or engraved line 507 indicating the maximum angle at which the drill guide 500 can be rotated via handle 510. When the surgeon sees the proximal edge 512 of the marking aligned with an upper surface 514 of bone plate 506 the surgeon will know that the maximum angulation has been reached. Note one or more additional parallel lines 507 could be added with each line indicating a different angle, for example 5, 10 or 15 degrees.

Figure 14:
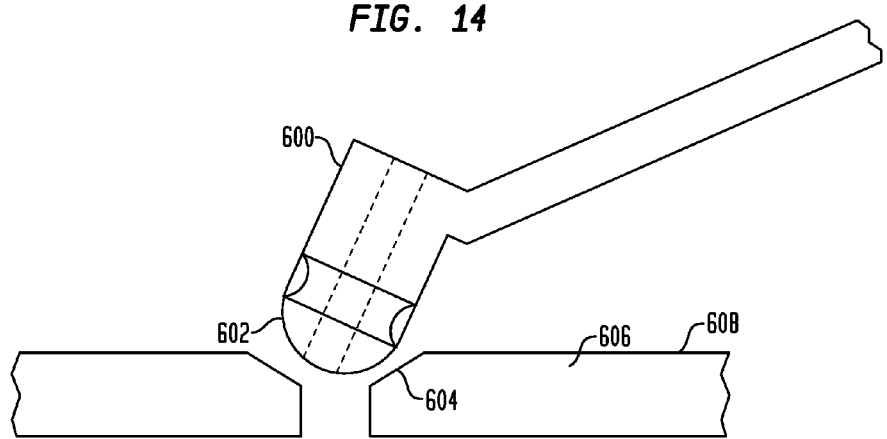
FIG. 14 is a cross-sectional view of yet another embodiment of the present invention.

Referring to FIG. 14 there is shown a drill guide 600 which is similar to the aforementioned drill guides but having a part-spherical distal end 602 for engaging a conical counterbore 604 in a plate 606. This embodiment illustrates the possibility that the geometry of the distal end, for example 602 of drill guide 600 can be different than the shape of a counterbore such as 604. As long as the distal end of the drill guide can rotate in the counterbore to the point where one of the above-mentioned indicators lines up with the top surface 608 of a bone plate such as 606 then such a combination can be utilized. Obviously other markers may be used which can either be seen or felt by the surgeon to indicate the alignment of the marker with the top surface of the bone plate when in a position of a maximum angulation of the drill guide to place the screw head at or below the surface of the plate. Specifically a two color system could be used with the leading or distal end of the gauge having a highly visible color at or above the line so that the surgeon would need to see all the color above the top plate surface to insure the maximum angle had not been exceeded. Also different surface textures could be utilized instead of different colors.

Also, should it be acceptable for the screw head to sit above the outwardly facing surface of the bone plate then the gauge element may be located at a distance from the bottom end, of the shaft which contacts the counterbore surface which is greater than the distance from the outer plate surface to the bottom of the counterbore.

Although the invention herein has been described with reference to particular embodiments, it is to be understood that these embodiments are merely illustrative of the principles and applications of the present invention. Specifically the drill guide can be used with any plate being attached to a subsurface, such as a metal plate to wood, to insert the head of the screw is at or below the top surface of the plate when the screw is inserted at an angle. It is therefore to be understood that numerous modifications may be made to the illustrative embodiments and that other arrangements may be devised without departing from the spirit and scope of the present invention as defined by the appended claims.

The invention claimed is:

1. A method for inserting a bone screw through a hole in a bone plate and into bone at a maximum angulation of a bone screw central longitudinal axis with respect to a central axis of the hole, comprising:

placing a bone contacting surface of a bone plate on a bone surface, the bone plate having at least one screw hole surrounded by a recessed part-spherical surface formed in an outermost surface of the bone plate opposite the bone contacting surface;

the screw hole extending from a base of the recessed part-spherical surface to the bone contacting surface along a central axis;

inserting an instrument having a distal portion into the recessed part-spherical surface surrounding the plate hole, the instrument distal portion including a guide bore extending along an axis, a circumferentially extending gauge element, the gauge element spaced proximally from a distal most surface of the instrument distal portion, where the distal most surface contacts a base of the recessed part-spherical surface, the spacing of the gauge element from the distal most surface of the instrument is less than or equal to a distance from the base of the recessed part-spherical surface to the outermost surface of the bone plate so that the gauge element is at or below the plate outermost surface when the gauge element guide bore axis is rotated up to 10° from a coaxial position with respect to the central hole axis;

tilting the inserted instrument about the central axis of the bone plate hole to the angle of up to 10° wherein the gauge element remains at or below an outermost surface of the bone plate which is adjacent the recessed part-spherical surface;

drilling a hole in the bone through the guide bore in the instrument; and inserting a bone screw into the bone plate screw hole.

2. The method as set forth in claim 1 wherein the gauge element is an indicator extending around a circumference of the instrument distal portion.

3. The method as set forth in claim 2 further comprising tilting the instrument to a maximum angle that maintains the circumferential indicator at or below the outermost surface of the bone plate surrounding the recessed part-spherical surface.

4. The method as set forth in claim 3 wherein the maximum angle of instrument tilt which maintains the circumferential indicator below the outer surface of the bone plate is 10°.

5. The method as set forth in claim 3 wherein the maximum angle of tilt is 10°.

6. The method as set forth in claim 4 wherein the instrument is tilted by manipulating a handle attached to the distal portion of the instrument.

7. The method as set forth in claim 1 wherein the distal portion of the instrument has a distal most surface which is part-spherical in shape.

8. The method as set forth in claim 2 wherein the indicator extends around the entire circumference of the distal portion of the instrument.

9. The method as set forth in claim 8 wherein the guide bore in the distal portion of the instrument extends perpendicular to a plane containing the entire circumference of the indicator.

10. The instrument as set forth in claim 3 wherein the circumferential indicator is formed entirely around a cylindrical portion of the instrument distal portion, the cylindrical portion having a diameter equal to a maximum diameter of the distal portion part-spherical section.

11. The method as set forth in claim 1 wherein the recessed part-spherical surface has a concave surface surrounding the at least one screw hole in the bone plate.

12. The method as set forth in claim 11 wherein the instrument distal portion has a leading end including a part-spherical convex surface for contacting the recessed part-spherical concave surface surrounding the at least one screw hole.

13. The method as set forth in claim 12 wherein the instrument distal portion proximal of the leading end is cylindrical, with the cylinder having a diameter equal to the largest diameter of the part-spherical convex surface of leading end.

14. A method for inserting a bone screw through a bore in a bone plate and into a bone at a maximum angulation of a bone screw central longitudinal axis with respect to a central axis of the hole, comprising:

obtaining a bone screw having a head and a shaft;

placing a bone plate on a bone surface, the bone plate having at least one bore surrounded by a recessed part-spherical surface, the bone plate having a bone contacting surface and an outwardly facing surface spaced therefrom;

placing a drill guide having a guide bore extending along an axis and having a distal portion with a curved contact surface formed on a distal end thereof on the recessed part-spherical surface of the bone plate, the drill guide distal portion having a circumferential marking extending around a cylindrical surface of the distal portion, the bone screw head having a height corresponding to the marking, the circumferential marking spaced from a distal most surface of the drill guide distal portion a distance less than the distance from a surface of the recessed part-spherical surface closest to the bone-contacting surface to the outermost bone plate surface so that pivoting the drill guide bore axis with respect to the central axis of the hole to a predetermined angle locates the marking at or below the outermost surface of the bone plate;

tilting the drill guide bore axis with respect to the central axis of the bone plate hole to the predetermined angle so that the circumferential marking is at or below the outermost outwardly facing surface of the bone plate;

drilling a hole in the bone through a bore in the drill guide; and inserting a bone screw into the bone plate hole at the predetermined angle so the bone screw head contacts the recessed part-spherical surface.

15. The method as set forth in claim 14 wherein the maximum angle of tilt is 10°.

\* \* \* \* \*